United States Patent [19]

Chuter

[11] Patent Number: 5,456,713
[45] Date of Patent: Oct. 10, 1995

[54] EXPANDABLE TRANSLUMINAL GRAFT PROSTHESIS FOR REPAIRS OF ANEURYSM AND METHOD FOR IMPLANTING

[75] Inventor: Timothy Chuter, Pittsford, N.Y.

[73] Assignee: Cook Incorporated, Bloomington, Ind.

[21] Appl. No.: 159,774

[22] Filed: Nov. 30, 1993

Related U.S. Application Data

[63] Continuation of Ser. No. 782,696, Oct. 25, 1991, abandoned.

[51] Int. Cl.⁶ .............................. A61F 2/06; A61M 29/02
[52] U.S. Cl. .............................. 623/1; 606/194; 606/195
[58] Field of Search .................................... 623/1, 11, 12; 606/191, 192, 193, 194, 195–198; 604/96, 8; 600/36

[56] References Cited

U.S. PATENT DOCUMENTS

| | | | |
|---|---|---|---|
| 3,657,744 | 4/1972 | Ersek | 3/1 |
| 4,140,126 | 2/1979 | Chaudhury | 128/325 |
| 4,512,338 | 4/1985 | Balko et al. | 128/1 |
| 4,562,596 | 1/1986 | Kornberg | |
| 4,577,631 | 3/1986 | Kreamer | 623/1 |
| 4,580,568 | 4/1986 | Gianturco | 128/345 |
| 4,655,771 | 4/1987 | Wallsten | 623/1 |
| 4,733,665 | 3/1988 | Palmaz | 128/343 |
| 4,739,762 | 4/1988 | Palmaz | 128/343 |
| 4,740,207 | 4/1988 | Kreamer | 623/1 |
| 4,776,337 | 10/1988 | Palmaz | 128/343 |
| 4,787,899 | 11/1988 | Lazarus | 623/1 |
| 4,830,003 | 5/1989 | Wolff et al. | 128/343 |
| 5,104,399 | 4/1992 | Lazarus | |

FOREIGN PATENT DOCUMENTS

| | | | |
|---|---|---|---|
| 0423916 | 4/1991 | European Pat. Off. | |
| 0461791 | 12/1991 | European Pat. Off. | |
| 0508473 | of 1992 | European Pat. Off. | |
| 0472731 | 3/1992 | European Pat. Off. | 606/194 |
| 9112047 | 8/1991 | WIPO | 606/194 |

OTHER PUBLICATIONS

Mirich, D. et al., "Percutaneously Placed Endovascular Grafts for Aortic Aneurysms: Feasibility Study," *Radiology*, vol. 170, No. 3, Part 2, Mar. 1989, pp. 1033–1037.

Lawrence, David D. Jr. et al., "Percutaneous Endovascular Graft: Experimental Evaluation," *Radiology*, vol. 163, No. 2, pp. 357–360, May 1987.

Palmaz, Julio C. et al., "Expandable Intraluminal Vascular Graft: A Feasibility Study," *Surgery*, vol. 99, No. 2, pp. 199–205, Feb. 1986.

Dotter, Charles T. et al., "Transluminal Expandable Nitinol Coil Stent Grafting: Preliminary Report," *Radiology*, vol. 147, pp. 259–260, Apr. 1983.

Cragg, Andrew et al., "Nonsurgical Placement of Arterial Endoprostheses: A New Technique Using Nitinol Wire," *Radiology*, vol. 147, pp. 261–263, Apr. 1983.

Dotter, Charles T., "Transluminally-placed Coilspring Endarterial Tube Grafts," *Investigative Radiology*, vol. 4, No. 5, pp. 329–332, Sep.–Oct. 1969.

(List continued on next page.)

*Primary Examiner*—Randall L. Green
*Assistant Examiner*—Debra S. Brittingham
*Attorney, Agent, or Firm*—Richard J. Godlewski

[57] ABSTRACT

A transluminal grafting system for grafting a prosthesis to the wall of a lumen includes a tubular graft provided with spring assemblies and anchoring barbs. The prothesis is mounted on an apertured tubular carrier and a central control means is inserted into the bore of the apertured carrier. Mooring loops are attached to the prothesis, pass through the apertures of the tubular carrier, and engage the central control means. An introducer sheath covers the system for smooth insertion into a lumen. When the graft has been positioned, the central control means maintains the axial position of the prosthesis. When the introducer sheath is pulled, the prostheis is exposed and the spring assemblies return to an expanded state and anchor the graft against the internal wall of the lumen.

24 Claims, 9 Drawing Sheets

OTHER PUBLICATIONS

Palmaz, Julio C. et al., "Transluminal Bypass of Experimental Abdominal Aortic Aneurysm," R.S.N.A. 1990 Abstracts, p. 202, No. 695.

Carrasco, C. Humberto et al., "Gianturco Stent in Vena Caval Stenoses," R.S.N.A. 1990 Abstracts, p. 202, No. 696.

Inoue, Kanji et al., "Percutaneous Implantation of Aortic Endovascular Graft for Created Aneurysm: Animal Experiment," *Circulation* 1991, 84 (4 Suppl. II):II–421.

Cragg, A. H. et al., "Percutaneous Arterial Grafting", *Radiology*, vol. 150, No. 1, Jan. 1984, pp. 45–49.

Matsumae, M. et al., "An Experimental Study of a New Sutureless Intraluminal Graft With an Elastic Ring That Can Attach Itself to the Vessel Wall", *Journal of Vascular Surgery*, vol. 8, No. 1, Jul. 1988, pp. 38–44.

Mirich, D. et al., "Percutaneously Placed Endovascular Grafts for Aortic Aneurysms: Feasibility Study", *Radiology*, vol. 170, No. 3, Part 2, Mar. 1989, pp. 1033–1037.

Maass, D. et al., "Radiological Follow–up of Transluminally Inserted Vascular Endoprostheses: An Experimental Study Using Expanding Spirals", *Radiology*, vol. 152, No. 3, 1984, pp. 659–663.

Richter, G. M. et al., "Three–year Results of Use of Transjugular Intrahepatic Portosystemic Stent Shunt", R.S.N.A. 1991 Abstracts, p. 99, No. 63.

Richter, G. M. et al., "Superior Clinical Results of Iliac Stent Placement versus Percutaneous Transluminal Angioplasty: Four–year Success Rates of a Randomized Study", R.S.N.A. 1991 Abstracts, p. 161, No. 411.

Vallbracht, C. et al., "New PTFE Closed Stent: First Experimental Results", R.S.N.A. 1991 Abstracts, p. 161, No. 415C.

Wunderlich, C. C. et al., "Imaging of the Palmaz Stent in the Prostatic Urethra", R.S.N.A. 1991 Abstracts, p. 217, No. 734C.

Palmaz, J. C. et al., "Three–year Experience with Iliac Artery Stents", R.S.N.A. 1991 Abstracts, p. 224, No. 894.

EXPANDABLE TRANSLUMINAL GRAFT PROSTHESIS FOR REPAIRS OF ANEURYSM AND METHOD FOR IMPLANTING

This is a continuation of copending application Ser. No. 07/782,696 filed on Oct. 25, 1991, now abandoned.

FIELD OF THE INVENTION

The invention relates to transluminal graft prostheses for the repair of aneurysms and a method for implanting them.

BACKGROUND OF THE INVENTION

The abdominal aorta is prone to aneurysmal dilation between the renal and iliac arteries. The attenuated wall of the aneurysm is unable to withstand arterial pressures so that dilation tends to progress to a point where rupture is likely. The highly invasive procedure necessary for conventional repair of an aortic aneurysm consists of an abdominal incision, dissection of the arteries, and the interruption of blood flow to the lower body and legs while an artificial graft is implanted to bypass the aneurysm.

Such invasive surgical repair of vital lumens has profound undesirable effects on the respiratory and cardiovascular systems of elderly patients who typically require the operation. The operation is expensive and entails significant life threatening risk. It is therefore highly desirable to replace conventional surgical repair with a less traumatic, less complicated and safer procedure. The present invention serves these needs, and is particularly well adapted to reconstruction of an abdominal aortic aneurysm. The prosthetic graft of this invention will provide a resilient conduit, bridging the aneurysm and reducing the risk of rupture, without the attendant morbidity and expense of conventional surgical repair. The invention, however, is not limited to aortic aneurysm repair and has applications in a variety of situations in which corporeal lumen repair is required.

There are several devices already existing which are stated to be useful for the remote repair of corporeal lumens. U.S. Pat. No. 4,512,338, issued to Balko et al., discloses a device for transluminal repair of, and restoring patency of, a weakened or damaged corporeal vessel. The device consists of a nitinol wire, previously memory-shaped into a longitudinal coil, which is cooled and reformed into a straight wire and inserted into the vessel requiring repair. When placed in the body and stripped of heat insulating means, the wire warms and returns to its preselected coiled dimensions to support the vessel wall. Use of a device such as nitinol wire may be undesirable because there is a danger of possibly puncturing or lacerating the lumen wall during the emplacement process. Another problem lies in fitting the prosthesis to the vessel because the prosthesis does not assume its final shape (and length) until it is inside the artery. The exact position of both ends of the prosthesis is very important due to the proximity of vital arteries to the ends of the aneurysm. Yet another problem with these devices is the difficult task of attaching the sleeve to the wire support because the wire is many times longer than the sleeve at the time it is inserted.

U.S. Pat. No. 4,140,126, issued to Choudhury, discloses a device for repairing an aneurysm. The device is mounted on the outside of a carrier catheter, and is positioned in the vessel in a collapsed form, smaller in diameter than that of the vessel. The device is then expanded onto the vessel wall by means of a mechanical expanding apparatus which is controlled by the user from outside the body by means of a wire. Upon expansion, anchoring pins are driven into the vessel wall. The wire is positioned on the outside of the carrier catheter, and is held in place by passing through many slip rings, each of which is firmly attached to the catheter. The slip rings permit the wire to slide when remotely operated. The wire is also attached to the expanding means at its proximal (downstream) end by slip couplings which permit the wire and expansion means to pass through the couplings during the expansion process. This device is mechanically complex and may not apply sufficient force to drive the pins into an atherosclerotic aorta or seal the graft to the arterial lumen. Furthermore, there is nothing to shield the vessel wall from the sharp pins while the device is moving from the insertion point to the point of repair. The pins are interspaced in folds of the graft material and could protrude from these folds while the device is moved into position. This could result in damage to the vessel wall in locations remote from the repair.

U.S. Pat. No. 4,787,899, issued to Lazarus, describes a system of positioning a graft within a body lumen. The graft is loaded into a guide which is inserted into the lumen. An inflatable balloon is used to anchor the distal (upstream) end of the graft onto the wall of the lumen, and then the guide is pushed upstream, pulling the folded graft out of the guide and onto the wall of the lumen, where staples at the proximal (downstream) end anchor into the wall of the lumen. Because the graft is folded or crimped axially, there is no sure method of determining where the expanded graft will position itself on the wall of the lumen, other than by measuring from the point of initial contact on the wall. This is difficult to do utilizing the remote insertion procedure. Also, the balloon providing the anchor for the distal (upstream) end of the graft while the guide is moved upstream may not provide enough pressure on the wall of the vessel to prevent slippage which could result in misplacement of the graft. The axial crimping used in these grafts may not impart radial elasticity and standard graft materials may not have sufficient elasticity as an intrinsic property. The small amount of apparent elasticity present in knitted grafts is actually a form of deformability in that expansion in one direction is accompanied by contraction in another. This means that the "guide" should be very close in size to the lumen of the vessel. As such, it should be introduced directly into the vessel to be repaired, rather than via a distant (much smaller) vessel. Also, the large guide may be difficult to withdraw through the graft after placement since it presents an open edge which might catch on any irregularities of the lumen.

The report, *Percutaneously Placed Endovascular Grafts for Aortic Aneurysms: Feasibility Study,* from the Department of Diagnostic Radiology, University of Texas M.D. Anderson Cancer Center, printed in, 170 Radiology 1033–37 (1989), deals with a self-expanding graft consisting of several stents connected in a chain. Two stainless steel struts run down the length of the chain, forming a rigid structure along the longitudinal axis. The structure is partially covered in a secured nylon sheath, is compressed radially, and is introduced into a lumen via a catheter and a blunt-tipped introducer wire used to push the graft up the catheter and into position. Placement is secured by withdrawing the catheter while holding the introducer wire stationary. This device may be difficult to insert because a chain structure is difficult to push unless it is rigid. The rigidity would make it very difficult to negotiate femoral and iliac arteries which are frequently tortuous. Precise positioning of the graft could be impaired because the pusher wire is not attached to the graft. This poses the potential for mispositioning of the graft during the withdrawal of the sheath. Hemorrhage could also be a major problem with this method of introduction. The introducer sheath is carried into position on the outside of a dilator, which must be removed before the graft can be inserted, leaving the sheath as a conduit from the artery to the outside of the body. The need to introduce the graft complicates the use of hemostatic seals on the sheath. Only one of these grafts carried barbs. The other model showed a tendency to migrate. There is a possibility that the sheathed wall of the barbed device could be breached by the barbs during transfer of the graft to the point of repair because the graft is pushed through the entire length of the catheter with the springs expanded against the inner wall of the catheter. Also, the wide mesh of the material used may not form a barrier to blood leaks, so that the aneurysm could be exposed to arterial pressure.

OBJECTS AND SUMMARY OF THE INVENTION

The present invention provides a transluminal graft prosthesis that can be safely and precisely positioned.

An object of the present invention is to provide a prosthesis for the safe repair of aneurysms without the risks associated with invasive surgical repair.

It is another object of the invention to provide a coupling between a plurality of spring expanding assemblies that provides a relatively flexible prosthesis during insertion, a relatively rigid prosthesis after attachment, and also maintains the alignment of the springs when the prosthesis is compressed by an extrusion device applied to one end.

The present invention provides a device for transluminal grafting of a prosthesis in a lumen, comprising: a tubular introducer sheath having a longitudinal bore; a prosthesis comprising a tubular graft having a longitudinal bore and disposed in the longitudinal bore of the tubular introducer sheath, the graft being expandable radially to substantially conform to the interior wall of a lumen; a spring expanding assembly permanently attached to the tubular graft to expand the graft so that it substantially conforms to the interior wall of a lumen when the graft is removed from the introducer sheath; an anchoring means for permanently attaching the graft to an interior wall of a lumen; a tubular carrier means having a longitudinal bore and disposed in the longitudinal bore of the tubular graft, the tubular carrier means provided with a plurality of apertures; a central control means for maintaining the axial position of the prosthesis during removal of the introducer sheath, the central control means disposed in the longitudinal bore of the tubular carrier means; and mooring loops engaging the prosthesis and passing through the apertures in the tubular carrier means to engage the central control means.

The present invention also provides a method for engrafting a prosthesis in a lumen comprising the steps of a) providing an access to the lumen; b) providing a device for engrafting the prosthesis comprising: a tubular introducer sheath having a longitudinal bore; a tubular graft having a longitudinal bore and disposed in the longitudinal bore of the tubular introducer sheath, the graft being expandable radially to substantially conform to the interior wall of a lumen; a spring expanding assembly permanently attached to the tubular graft to expand the graft so that the graft substantially conforms to the interior wall of a lumen when the graft is removed from the introducer sheath; an anchoring means for permanently attaching the graft to an interior wall of a lumen; a tubular carrier means having a longitudinal bore and disposed in the longitudinal bore of the tubular graft, the tubular carrier means provided with a plurality of apertures; a central control means for maintaining the axial position of the prosthesis during removal of the introducer sheath, the central control means disposed in the longitudinal bore of the tubular carrier means; mooring loops engaging the prosthesis and passing through the apertures in the tubular carrier means to engage the central control means; c) inserting the device and urging the device into a lumen to a desired location within the lumen; d) withdrawing the tubular introducer sheath to expose the graft; e) disengaging the central control means from the mooring loops; and f) removing the tubular introducer sheath, carrier means, and central control means.

The present invention provides an occlusive umbrella comprising: a spring expanding assembly having a proximal and a distal end; barbs attached to the proximal end of the spring means; a tubular graft having a longitudinal bore and having a proximal end and a distal end, the tubular graft open at the proximal end and closed at the distal end, the graft attached to the spring; a dilator having a distal end and a proximal end, the proximal end of the dilator attached to the distal end of the tubular graft; a first tubular catheter having a proximal end, a distal end, and a longitudinal bore, the first tubular catheter inserted into the longitudinal bore of the graft and attached to the proximal end of the dilator; a second tubular catheter having a proximal end, a distal end, and a longitudinal bore, the distal end of the second catheter communicating with the proximal end of the first catheter; a flexible rod having a proximal end and a distal end, the distal end of the flexible rod inserted into the longitudinal opening of the first catheter and the longitudinal opening of the second catheter, the distal end of the flexible rod contacting the dilator head.

The present invention provides a flexible spring alignment and compression resistance assembly comprising: a first and second spring expanding assembly each having a plurality of apertures; a plurality of retaining shafts each having a first end and a second end, the shafts having a diameter equal to or smaller than the apertures of the first and second spring expanding assemblies, the first end of each of the retaining shafts slidably inserted into one of the apertures of the first spring expanding assembly and the second end of each of the retaining shafts slidably inserted into one of the apertures of the second spring expanding assembly, a first protrustion attached to each of said first ends and a second protrusion attached to each of said second ends, the protrusions larger than the apertures in the first and the second spring expanding assemblies to prevent the protrusions from passing through the apertures.

The present invention also provides a flexible spring alignment and compression resistance assembly comprising: a first spring expanding assembly having a plurality of apertures; a second spring expanding assembly; a plurality of retaining shafts each having a first end and a second end, the shafts having a diameter equal to or smaller than the apertures of the first spring expanding assembly, the first end of each of the retaining shafts slidably inserted into one of the apertures of the first spring expanding assembly and the second end of each of the retaining shafts attached to the second spring expanding assembly, a protrusion attached to each of said first ends, the protrustions larger than the apertures in the first spring expanding assembly to prevent the protrusions from passing through the apertures.

The invention is described in greater detail below based on a few selected embodiments. Those skilled in the art will appreciate that the prosthesis according to the invention can be applied in various modifications.

BRIEF DESCRIPTION OF THE DRAWINGS

FIG. 9-A is a longitudinal cross-sectional view of two compressed spring expanding assemblies connected by the flexible spring alignment and compression resistance assembly of FIG. 7.;

FIG. 9-B is a longitudinal cross-sectional view of two uncompressed spring expanding assemblies connected by the flexible spring alignment and compression resistance assembly of FIG. 7;

DETAILED DESCRIPTION OF THE INVENTION

Figure 1:
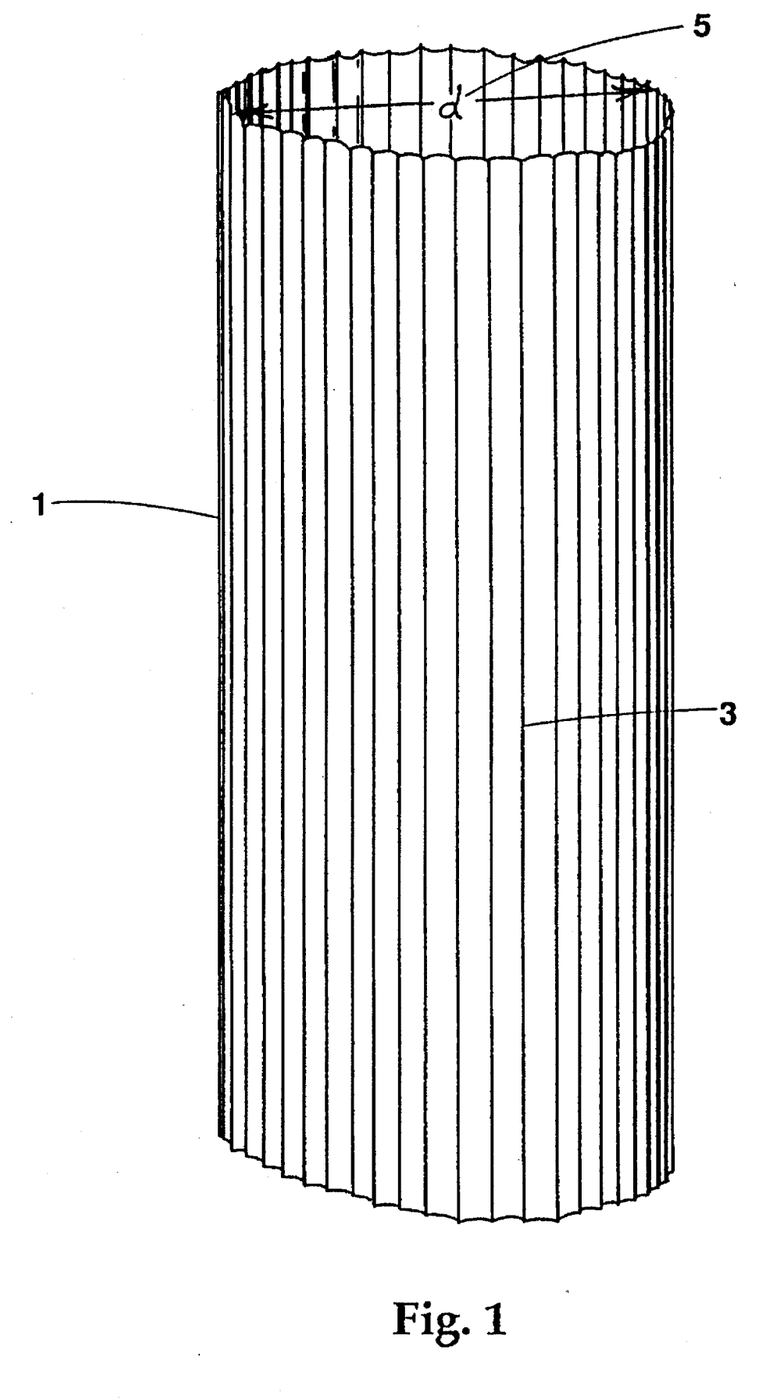
FIG. 1 is a side-view of a tubular graft of the instant invention.

The graft 1 shown in FIG. 1 is in the form of an elongated cylindrical tube defining a longitudinal bore that is multiply crimped 3, or folded over to facilitate the compression and expansion of the graft as the diameter 5 of the graft decreases and increases. Transverse elasticity may also be achieved or enhanced through inherent properties of either the weave or constituent fibers used to construct the graft 1. The graft 1 is preferably constructed from a material such as woven multifilament polyester (such as Dacron™), which is known to be sufficiently biologically inert, non-biodegradable, and durable to permit safe insertion inside the human body. Any material with such qualities may be used, however. Polyester is also known to excite fibrous ingrowth which will secure the graft 1 to the wall of the lumen within a few months of its insertion.

The typical graft 1 is of fixed length and relatively inelastic along its longitudinal axis. A variable length graft may also be used and could be constructed by either having two pieces of graft, one inserted within the other in a telescopic arrangement, capable of being manipulated within the body, or having one continuous piece of material that is folded back on itself. A spring within this area of the graft ensures apposition of the various layers at this level; the outer layers having a slightly smaller maximum diameter to provide a buttress against which the spring can expand in the absence of a secure arterial wall. Variability in length may also be achieved by providing elasticity along the longitudinal axis of the graft as a property of graft material or by having one or more elastic sections of such material within the main body of the graft.

Figure 2:
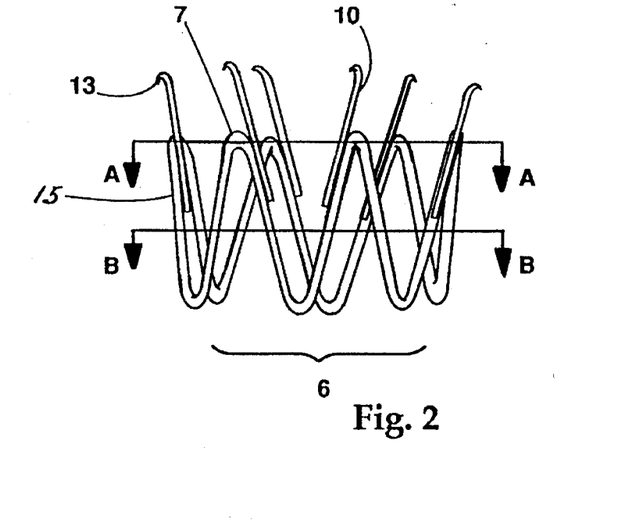
FIG. 2 is a side-view of a spring expanding assembly of the instant invention.
Figure 3:
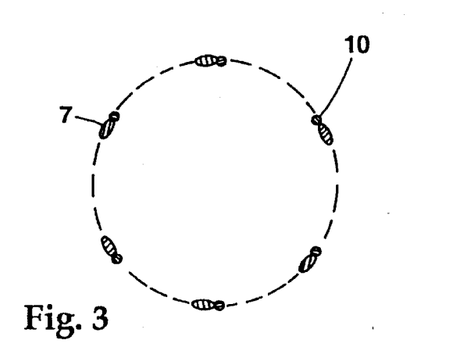
FIG. 3 is a top cross-sectional view of a spring expanding assembly shown in FIG. 2 taken along A—A.
Figure 4:
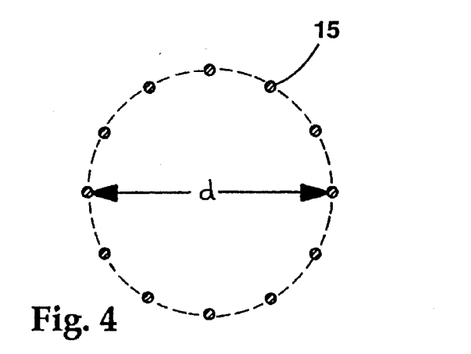
FIG. 4 is a top cross-sectional view of a spring expanding assembly shown in FIG. 2 taken along B—B.
Figure 5A:
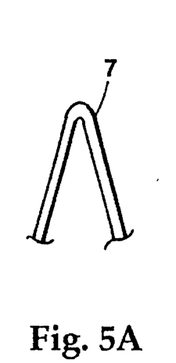
FIG. 5 is a side-view of alternative elbows of the spring expanding assembly of the instant invention.
Figure 5B:
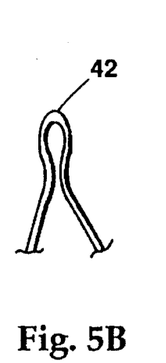
Figure 5C:
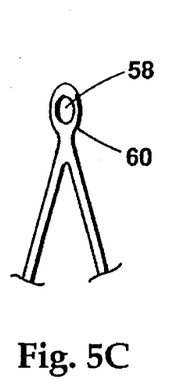
Figure 6:
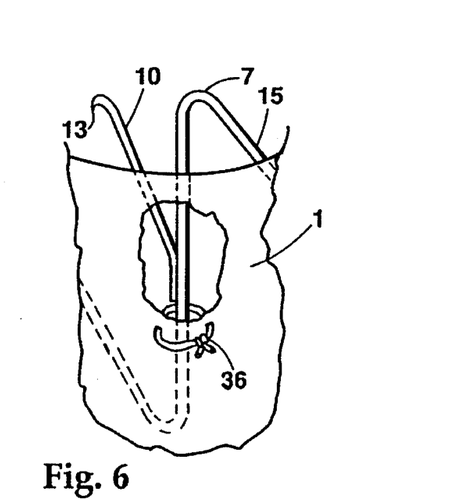
FIG. 6 shows a spring expanding assembly (with a barb attached) sutured to the graft.

The spring assembly 6 of FIG. 2 includes arms 15 which are bent to form elbows 7. Surgical barbs 10 having sharp tips 13 are attached to the arms 15 and protrude from the elbows 7. FIG. 3 is a top cross-sectional view of the spring assembly 6 of FIG. 2 taken along A—A showing six elbows 7 and associated barbs 10. FIG. 4 is a top cross-sectional view of the spring assembly 6 taken along B—B showing twelve arms 15 which extend from the six elbows 7 shown in FIGS. 2 and 3. A spring assembly 6 is typically formed from a continuous piece of fine gauge stainless steel spring wire that, if opened out, would appear in the shape of a zig-zag with multiple elbows 7. FIG. 5 shows that these elbows 7 may be simple arches 7, recurved arches 42, or apertured 60. The advantage of simple arches 7 is that the spring assembly 6 expands the longitudinal aperture of the graft 1 more evenly. The advantage of the recurred arches 42 is that they collapse more readily and are more durable. The apertured elbows 60 are used in the flexible spring alignment and compression resistance assembly. The two ends of the piece of bent wire are permanently attached end-to-end so as to form a circular structure, e.g., FIGS. 2, 3 and 4. FIG. 6 shows a portion of the spring assembly 6 with a barb 10 attached to an arm 15 of the spring assembly 6. The spring assembly 6 is sutured to the graft 1 with a non-biodegradable thread 36. The spring assembly 6 may also be constructed out of other inert metals such as titanium, or a plastic. When expanded, the spring assembly 6 is circular in shape when viewed from above, and may have a diameter, when in a relaxed state, equal to approximately twice the diameter of a lumen into which the graft 1 is to be inserted. The spring assembly 6 is typically attached to the inside of the cylindrical graft 1 at the distal (upstream) end or both ends of the graft 1 by sutures 36 of non-biodegradable material. The sutures 36 attach to the spring assembly 6 in such a way that the majority of the spring assembly 6 is covered by the graft material 1. Other embodiments may incorporate spring assemblies 6 being attached to the outside of the tubular graft 1 which would present a smoother surface to the flowing blood but has the drawback that the graft 1 would be in less intimate contact with the wall of the lumen.

The spring assembly 6 on the distal (upstream) end of the graft 1 has small surgical barbs 10 firmly attached to the spring assembly 6. The spring assembly 6 at the proximal (downstream) end of the graft may also be provided with barbs. The attachment of the barbs 10 to the graft 1 or spring assembly 6 must be permanent and can be either welded, brazed, or coupled in a fashion that is both biologically acceptable, and yet strong enough to withstand long-term stress. These barbs 10 spread radially outward from the longitudinal axis of the graft 1, such that when the spring assembly 6 opens inside the lumen, the barb tips 13 will come into contact with and engage the wall of the blood vessel to be repaired. The barb tips 13 will become imbedded in the wall through both the driving action of the spring assembly 6 and the pressure created by the flow of blood through the graft 1. The barb tips 13 are sharp and may be curved slightly downward toward the graft 1 to provide a more secure anchor in the direction of blood flow. The barbs 10 are positioned so that they are further upstream than the elbows 7 of the distal (upstream) spring assembly 12, and are of such a size that the wall of the blood vessel is not punctured or pierced when the barb tips 13 are firmly embedded therein. Attaching the barbs 10 to the spring assembly 6 via shafts bonded to the spring assembly 6 at the middle of one of the two arms 15 extending from an elbow 7 of the spring assembly 6 permits the barb tip 13 to slightly retract or rotate when compressed for loading into the introducer sheath 4 (as best seen in FIG. 6).

Figures 7, 8:
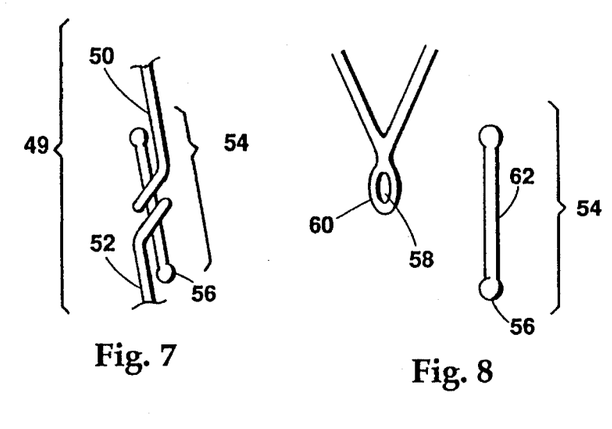
FIG. 7 is a side-view of a flexible spring alignment and compression resistance assembly.
FIG. 8 shows the elbow and retaining bar of the flexible spring alignment and compression resistance assembly of FIG. 7.

Though the spring assembly 6 is typically sutured only to the ends of the graft 1, several such spring assemblies 6 may also be connected to one another for added strength. This is necessary in embodiments of the prosthesis that require the graft to resist compression during removal from the introducer 4. Some flexibility is retained by connecting the spring assemblies 6 to each other in a way that permits separation (but not overlapping or misalignment) of adjacent spring elbows 60. FIG. 7 illustrates such a flexible spring alignment and compression resistance assembly 49 and shows a first spring arm 50 and a second spring arm 52 connected via a retaining bar 54. The retaining bar 54 is constructed of fine gauge wire with a protrusion 56 at each end. FIG. 8 shows a modified elbow 60 and includes an aperture 58 provided to receive the retaining bar 54. The retaining bar 54 slides through apertures 58 provided in the modified elbows 60 of adjacent arms 50 and 52. The rigidity of the retaining bar 54 prevents overlapping during compressive loading of the prosthesis, while the protrusions 56 prevent disassociation of the joints during flexion of the graft which might otherwise disrupt the chain of springs 50 and 52. The shaft 62 of the retaining bar 54 has a diameter slightly smaller than aperture 58 and the protrusion 56 has a diameter slightly larger than the aperture 58. The slidably mounted retaining bars 54 allow arms 50 and 52 to separate but prevents arms 50 and 52 from sliding over one another.

Figure 9A:
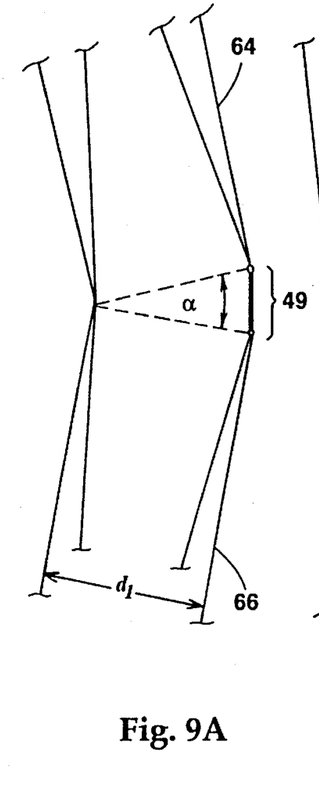
Figure 9B:
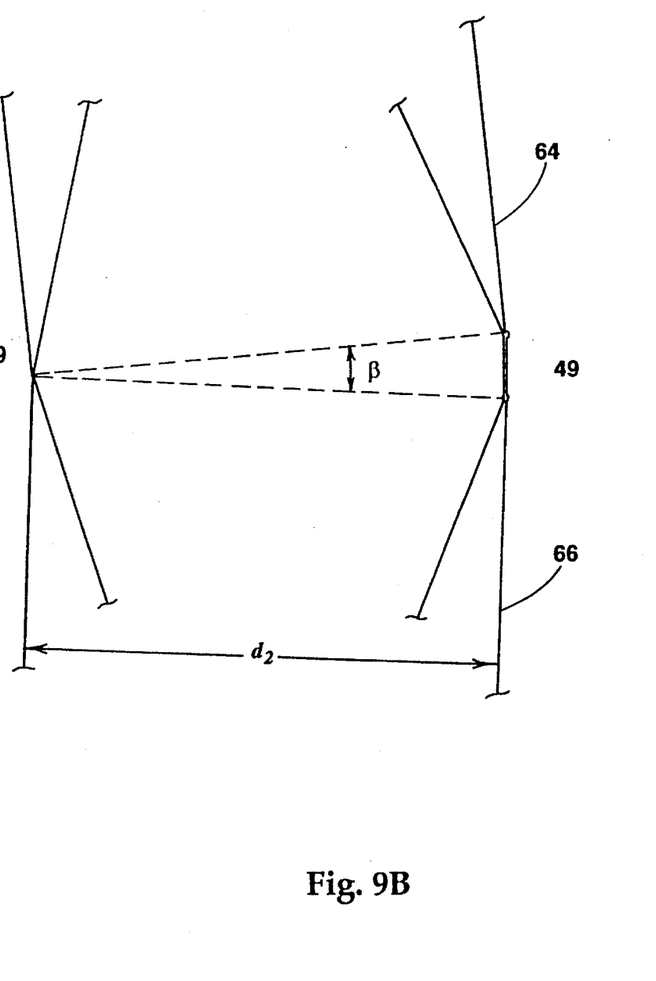

It is desirable that the joint between the spring assemblies 6 be flexible during introduction and relatively rigid once the graft has been implanted. As shown in FIGS. 9-A and 9-B, the joint is more flexible when the spring assemblies 64 and 66 are compressed (i.e., during insertion) and relatively rigid when the spring assemblies 64 and 66 are in an uncompressed state (i.e., after implantation). FIGS. 9-A and 9-B show a first spring assembly 64 connected to a second spring assembly 66 by a flexible spring alignment and compression resistance assembly 49. FIG. 9-A shows the spring assemblies 64 and 66 in a compressed state and FIG. 9-B shows the spring assembles 64 and 66 in an uncompressed state. Angle $\alpha$ represents the maximum angle between spring assemblies 64 and 66 when the springs are in a compressed state and angle $\beta$ represents the maximum angle between spring assemblies 64 and 66 when the springs are in an uncompressed state. Thus, the angle between spring assemblies 64 and 66 decreases with an increase in the transverse diameter of spring assemblies 64 and 66. The angle of flexion will be largest when spring expanding assemblies 64 and 66 are in a compressed state (diameter $d_1$) and the angle of flexion will be smallest when spring expanding assemblies 64 and 66 are in an uncompressed state (diameter $d_2$). Thus, because $\alpha$ is larger than $\beta$, the prosthesis becomes more rigid as its diameter increases. During insertion, the graft 1 is confined within the introducer sheath 4 and remains both narrow and flexible. After removal from the sheath 4 the graft 1 expands becoming more rigid.

Figure 10:
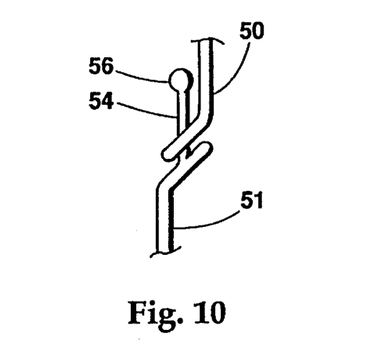
FIG. 10 is a side-view of a flexible spring alignment and compression resistance assembly and shows the retaining bar rigidly attached to one of the spring expanding assemblies.

The retaining bar 54 may also be non-slidably attached at one (but not both) of its ends to one of the spring expanding assemblies 51 as shown in FIG. 10.

Figure 11:
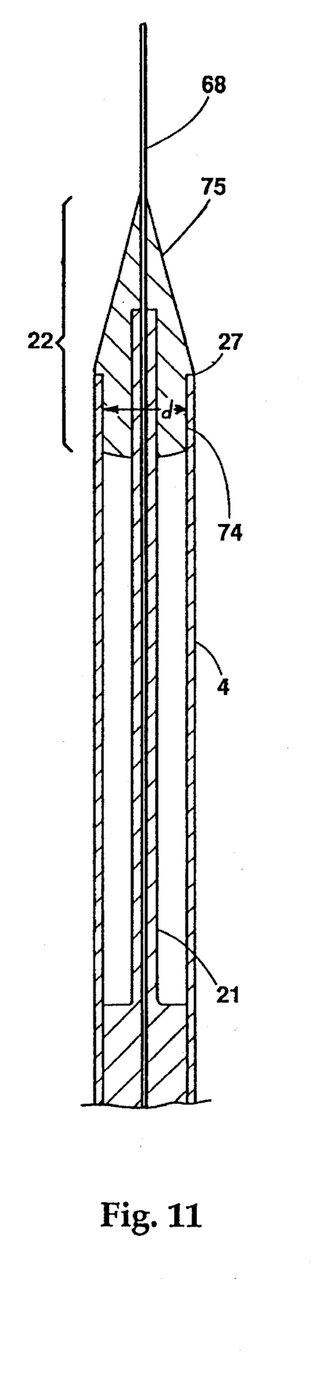
FIG. 11 is a longitudinal cross-sectional view of a tubular carrier of the instant invention shown with a dilator head at the distal (upstream) end.

FIG. 11 shows a tubular carrier 21 which has a dilator head 22 mounted at the distal (upstream) end. The dilator head 22 may have a distal (upstream) conical portion 75 and a proximal (downstream) cylindrical portion 74. The dilator head 22 may have a soft tipped guide-wire 68 protruding from its distal (upstream) end. The cylindrical portion 74 of the dilator 22 has a diameter d equal to the internal diameter of the introducer sheath 4.

Figure 12:
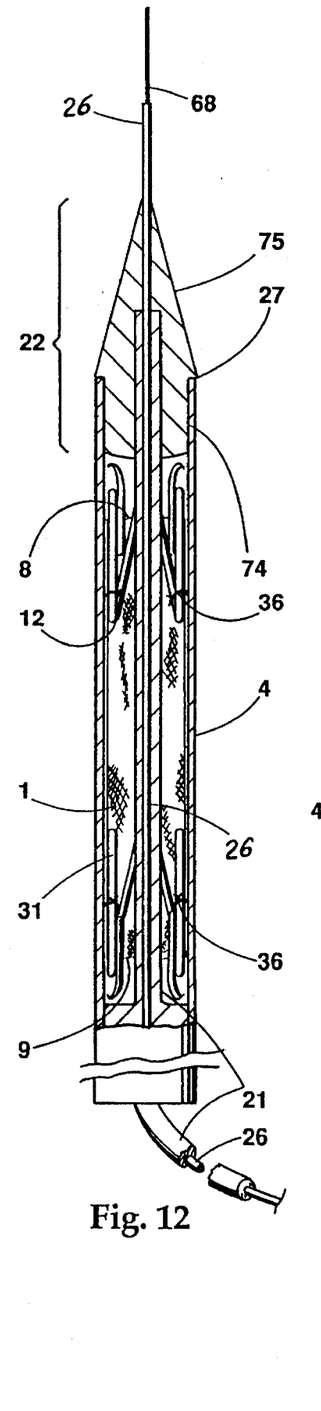
FIG. 12 is a longitudinal cross-sectional view of a "muzzle loading" apparatus of the instant invention.
Figure 13:
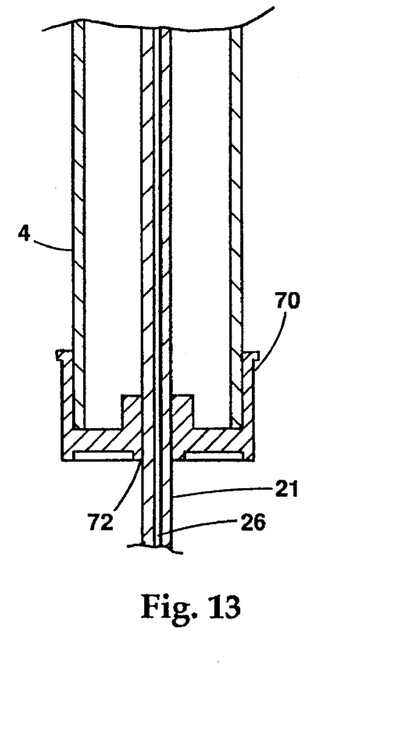
FIG. 13 is a longitudinal cross-sectional view of the proximal (downstream) end of the introducer sheath.

FIG. 12 shows the assembled "muzzle loading" apparatus and includes a tubular carrier 21 with a dilator head 22 at the distal (upstream) end; dilator head lip 27; introducer sheath 4; graft 1 which is slid on to the tubular carrier 21; distal (upstream) spring assembly 12; proximal (downstream) spring assembly 31; central control means 26 which is inserted into the tubular carrier 21; distal (upstream) end 8 of the graft 1; proximal (downstream) 9 end of the graft 1; and non-biodegradable sutures 36 that permanently attach the spring assemblies 12 and 31 to the graft 1. If the outer diameter of the tubular carrier 21 is equal to the internal diameter of the introducer sheath 4 leakage of blood between the two is minimal. Alternatively, the introducer sheath 4 may be closed at its proximal (downstream end) by a small rubber seal 70 as shown in FIG. 13 which has an aperture 72 for receiving the carrier 21.

"Muzzle loading" involves inserting the graft 1, already mounted on the tubular carrier 21, into the distal (upstream) end of the introducer sheath 4 before insertion of the introducer sheath 4 into the lumen. "Breech loading" involves inserting the graft 1 into the introducer sheath 4 from the proximal (downstream) end of the sheath 4, after the introducer sheath 4 has been inserted into the patient and is in position.

"Muzzle loading" has two main advantages that make it the preferred means of operation. The first advantage of "muzzle loading" over "breech loading" is the lower probability of hemorrhage. In the "breech loading" technique, the dilator 22 must be removed before the graft 1 can be inserted leaving the introducer sheath 4 as a large conduit between the arterial circulation and the outside of the body. Any effective seal in the introducer sheath 4 will obstruct insertion of the graft 1 unless this is carried within a second sheath (with the consequent increase in size.) The only other way to control the hemorrhage is to clamp the introducer sheath 4 on the outside, however, clamping is unlikely to be totally occlusive and may damage the introducer sheath 4. Moreover, the clamp must be removed to allow passage of the graft 1 which produces another period of rapid hemorrhage.

The second advantage of "muzzle loading" over "breech loading" is that if a single sheath 4 is to be used in the "breech loading" technique the graft 1 must be placed within the introducer 4 at the time of operation. This can be a tricky procedure especially when the outer end of the introducer sheath 4 is issuing a continual stream of blood.

Figure 14:
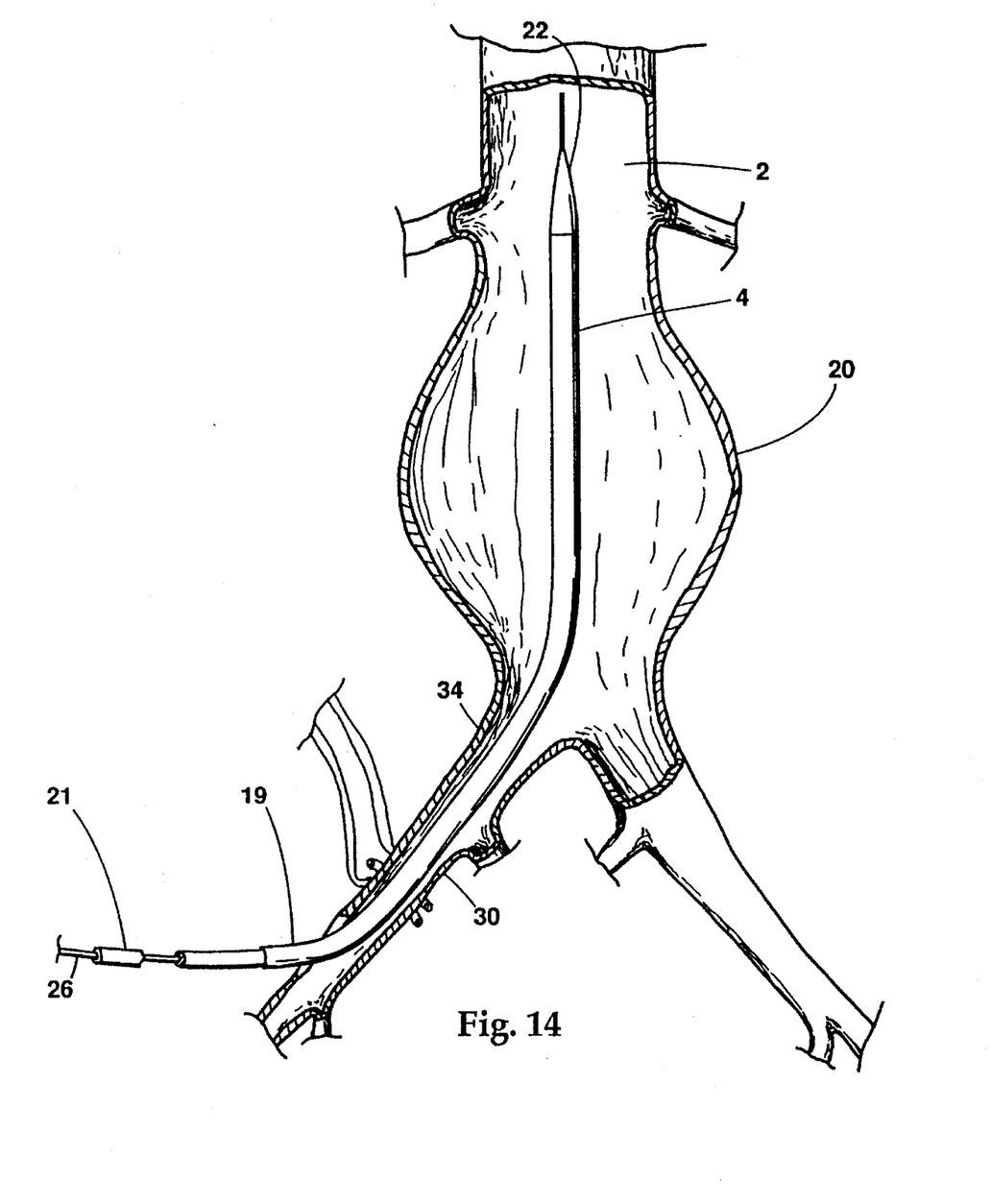
FIG. 14 is a longitudinal cross-sectional view of the aorta and iliac arteries and shows a dilator head, introducer sheath, tubular carrier, arteriotomy, and central control means.
Figure 15:
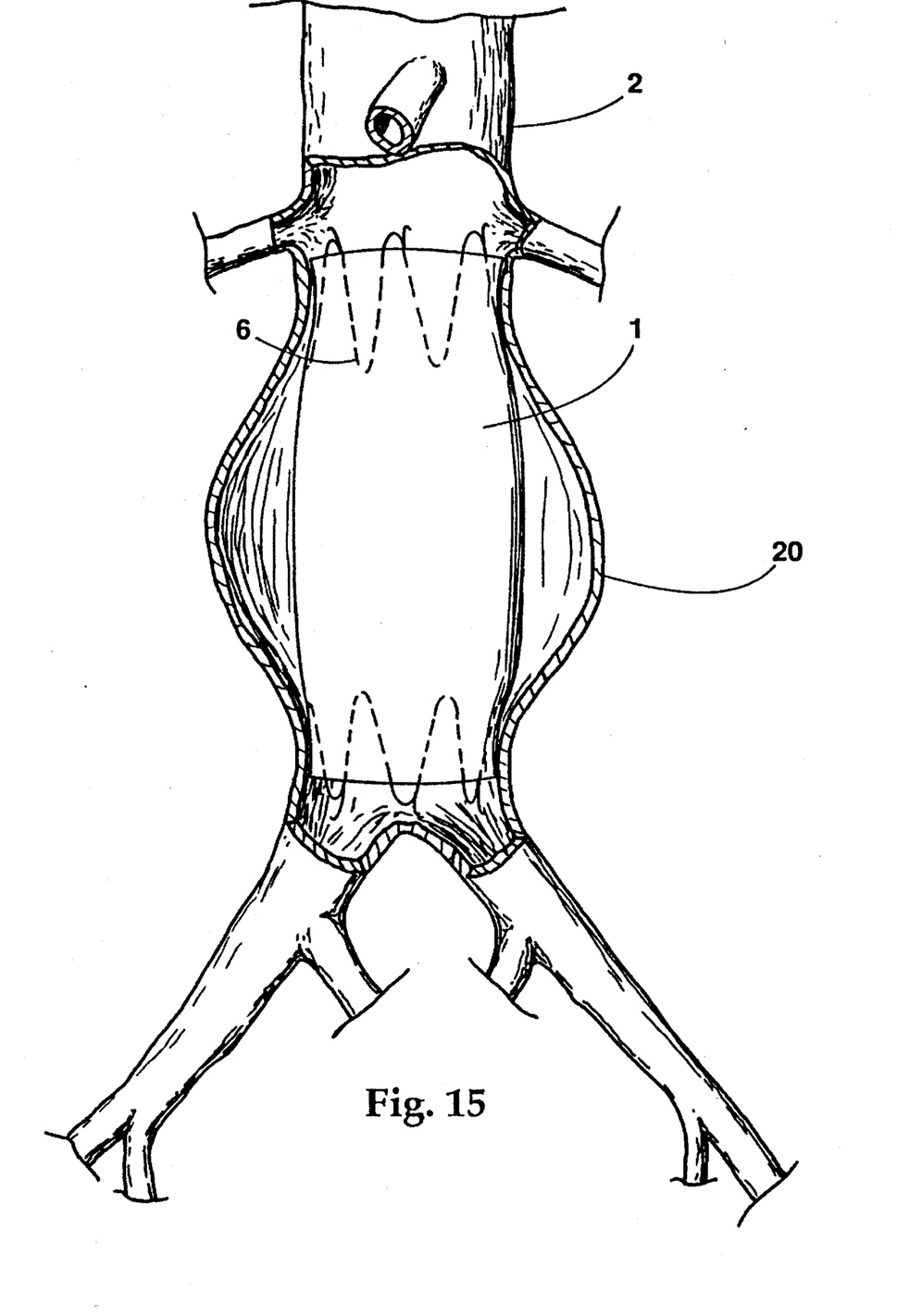
FIG. 15 is a longitudinal cross-sectional view of the aorta and iliac arteries and shows a graft implanted in the aorta on either side of an aneurysm.

FIG. 14 shows the common femoral artery 30; proximal (downstream) end 19 of introducer sheath 4; tubular carrier 21; iliac artery 34; aorta 2; aortic aneurism 20; dilator head 22; and central control means 26. FIG. 15 shows the graft 1 implanted in the aorta 2 at the site of the aortic aneurysm 20.

In the "muzzle loading" technique the graft 1 is inserted into the distal (upstream) end of the introducer sheath 4. The introducer sheath 4 is thin walled, smooth, flexible, sterilizable, non-toxic, and is tubular in form. The tubular carrier 21 fits inside the introducer sheath 4. A close match between the sizes of the sheath 4 and carrier 21 helps to eliminate any buckling of the tubular carrier 21 within the sheath 4 while simultaneously limiting the seepage of blood between the carrier 21 and the sheath 4. The tubular carrier 21 has a dilator 22 attached to the distal (upstream) end which has a conical tip 75 to facilitate the atraumatic passage of the apparatus from the groin into the upper end of the aneurysm. The dilator 22 is also provided with a cylindrical portion 74 on its proximal (downstream) end which mates with the introducer sheath 4.

The introducer sheath 4 fits over the cylindrical portion 74 of the dilator head 22. A tiny lip 27 at the junction between cylindrical portion 74 and conical portion 75 of the dilator head 22 overlaps the end of the introducer sheath 4 so that no edges are presented to the arterial lumen (or the thrombus that lines the aneurysm) during introduction of the apparatus. This reduces the trauma to vessels and minimizes the chance of dislodging a piece of thrombus that could embolize into the kidneys or lower limbs.

The central control means 26 may take the form of a catheter which extends the entire length of the carrier to the tip of the dilator head 22, so that its lumen can be used for the injection of angiographic dye, or as a means of threading the apparatus over a previously placed guide wire. Alternatively, the central control means 26 may pass all the way through the dilator head 22 and slide back and forth within the carrier 4 so that it may function as a guide wire itself. This has been found to be a useful in the technique of percutaneous insertion.

In the "breech loading" device, the introducer sheath 4 is a tubular structure having a uniform-diameter and is made of the same material as the "muzzle loading" introducer sheath 4. With this design, the tubular carrier 21 does not have a dilator 22, because the introducer sheath 4 can be carried into position around a standard dilator, which would then be removed before insertion of the tubular carrier 21 with the graft 1.

Figure 16:
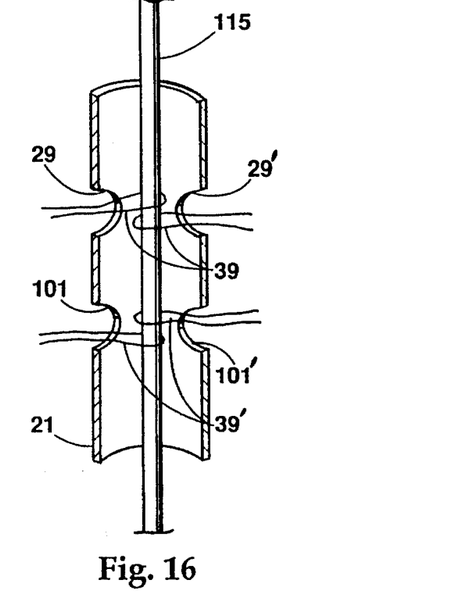
FIGS. 16 and 17 are longitudinal cross-sectional views of an apertured tubular carrier showing mooring loops and central control means.

FIG. 16 shows the tubular carrier 21, mooring loops 39 and 39'; central control wire 115; and apertures 29, 29', 101, and 101' in the wall of tubular carrier 21.

Figure 17:
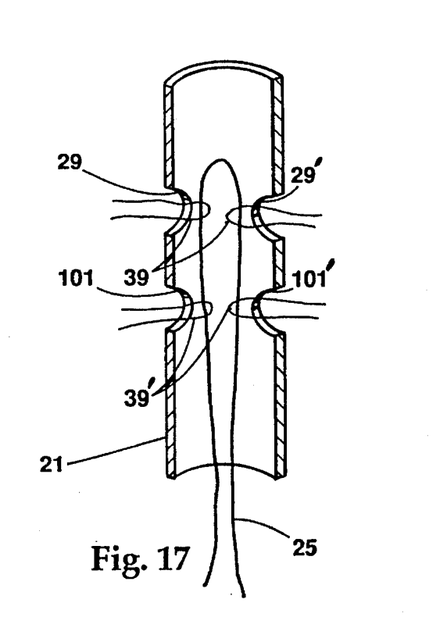

FIG. 17 shows the tubular carrier 21; mooring loops 39 and 39'; apertures 29, 29', 101 and 101' in the wall of the tubular carrier 21; and central control thread 25.

All "muzzle loading" (and some "breech loading") devices use a central control means 26 that runs up the center of the tubular carrier 21, to which the graft 6 may be moored, and which is used for maintaining the axial position of the graft 1 during removal of the introducer sheath 4. This central control means 26 can take one of several forms, including a flexible shaft 115 (such as a stainless steel wire or a narrow catheter) (as shown in FIG. 16) or a simple thread 25 (as shown in FIG. 17) that passes up the center of the tubular carrier 21, through the mooring loops 39 and 39', and then doubles back through the center of the tubular carrier 21 to its point of origin outside the patient. In the absence of mooring loops 39 and 39', this thread 25 can exit an aperture (29 29', 101 and 101'), pass through an elbow 7 of the spring assembly 6, traverse the apertures to the opposite elbow 7 of the spring assembly 6 (which it also encircles) pass back into the lumen of the carrier 21 through an aperture (29, 29', 101, and 101') and thereby return to the proximal end of the catheter 21. Release of the mooring loops 39 and 39' is accomplished by withdrawing the central control shaft 115 from the tubular carrier 21 or by releasing one end of the central control thread 25, which is then removed from the tubular carrier 21. If each end of the graft 1 is desired to be controlled and positioned independently of the other, the central control shaft 115 can be partially withdrawn to a point in between the two sets of mooring loops 39 and 39'. If the central control means 26 is a central control thread 25 (instead of a flexible shaft 115) multiple threads 25 can be used, one for each set of mooring loops 39 and 39'.

Because it has no dilator head, the carrier of the "breech loading" device need not traverse the graft 1 to the distal (upstream) end of the introducer sheath 4. Instead, it can end at the graft 1 which would be pushed rather than pulled from the sheath 4. No attachment to the graft 1 would then be needed, but the graft 1 would have to be more rigid and placement would be less precisely controlled.

The "muzzle loading" method will now be described. To assemble the apparatus prior to insertion, the central control means 26 is inserted through the entire length of the tubular carrier 21, which, in turn, is inserted through the entire length of the introducer sheath 4. With the end of the tubular carrier 21 and central control means 26 protruding past the top of the introducer sheath 4, the graft 1 is slid over the dilator head 22 and down the outside of the tubular carrier 21 until positioned directly below the tapered dilator head 22 of the tubular carrier 21. As shown in FIG. 16 the distal (upstream) of the graft 1 is then moored around the central control means 26 with a mooring loop 39 that engages the spring assembly 6, or is sutured to the graft 1. The mooring loop 39 enters the tubular carrier 21 via the aperture 29 and 29' and forms a mooring loop 39 which engages the central control means 26 so that the mooring loops 39 cannot exit the carrier 21 while the control means 26 occupies the longitudinal opening of the tubular carrier 21. These mooring loops 39 will remain attached to the graft 1 or springs 6 after placement of the graft 1. The mooring loops 39 are preferably made of a monofilament material of low thrombogenicity that in some applictions may be biodegradable. When the central control means 26 is withdrawn, mooring loops 39 are free to exit the tubular carrier 21. The proximal (downstream) end of the graft 1 can also be secured in the same manner through a second set of mooring loops 39' passing through a second set of apertures 101 and 101' in the tubular carrier 21, thereby facilitating independent positioning of the two ends of the graft 1. Once the graft 1 is compressed, the introducer sheath 4 is slid over the tubular carrier 21 and the edge of the introducer sheath 4 is fitted snugly against the lip 27 of the dilator head 22. The barbs 10 on the distal (upstream) spring assembly 12 are completely covered by the introducer sheath 4. The apparatus is now ready for insertion.

Figure 18:
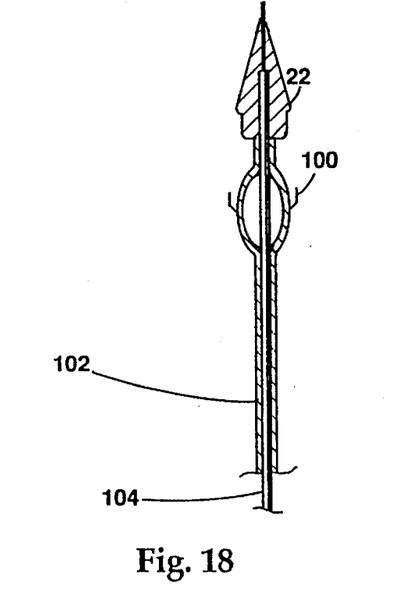
FIG. 18 is a longitudinal cross-sectional view of an alternative means of graft attachment.

FIG. 18 is a longitudinal cross-sectional view of an alternative embodiment of the carrier catheter that does not employ a central control means and shows cantilever hooks 100, outer carrier 102, inner catheter 104, and dilator head 22. In this embodiment, a pair of concentric catheters is bonded at the distal (upstream) end such that when the inner catheter 104 is pulled in the proximal (downstream) direction from outside the body, the outer catheter 102 bulges out. The graft 1 is held in position on the outer catheter 102 by means of cantilever hooks 100 attached to the outer surface of the outer catheter 102. These hooks 100 engage the spring assembly 6 of the graft 1 during insertion and prevent the graft 1 from changing its axial position while the introducer sheath 4 is withdrawn. The graft 1 is released from the hooks 100 when the outer catheter 102 is withdrawn.

These methods of securing the graft to the carrier for selective release are required because the outward expansion of the graft against the sheath generates considerable friction that must be overcome in order to extrude the graft. Without such a mechanism, the graft would move with the sheath and would be imprecisely extruded. In order to minimize the forces involved in extrusion, the sheath is constructed of a material (such as Teflon™) which has a low friction surface or is coated with a lubricous material (such as hydrogel polymer).

The insertion procedure may be a surgical procedure or may be accomplished percutaneously using a guide wire. In the surgical approach, for example, the femoral artery 30 is exposed through a short groin incision. Heparin is administered intravenously, hemostatic clamps or bands are applied, and the femoral artery 30 is opened. The complete apparatus is inserted into the open femoral artery 30, and is pushed through the femoral 30 and iliac 34 arteries into the aorta 2. The graft 1 is positioned so as to cover the entire length of the aortic aneurysm 20. Positioning is confirmed through fluoroscopy and angiography. Once the positioning has been confirmed, the introducer sheath 4 is pulled back exposing the distal (upstream) barbed spring assembly 12 and part of the length of the graft 1. The springs expand driving the barb tips 13 into the wall of the aorta 2. Once the entire graft 1 is out of the introducer sheath 4 the central control means 26 is withdrawn. As the central control means 26 is withdrawn past the point where the graft 1 is moored to the central control means 26 via the mooring loops 39, the mooring loops 39 will pass over the end of the central control means 26 and be free to pass through the apertures 29 and 29' in the tubular carrier 21. Blood flow in the aorta 2 aids in opening up the multiply crimped middle portion of the graft 1. Placement is performed in two stages. First, the introducer sheath 4 is withdrawn to expose the distal (upstream) 8 half of the graft 1 which expands and attaches to the wall of the aorta 2. The central control means 26 is then withdrawn to a point between the holes 29 and 29' and 101 and 101' in the tubular carrier 21, leaving only the proximal (downstream) 9 end of the graft 1 attached to the carrier 21. The proximal (downstream) 9 end of the graft 1 can then be positioned independently of the distal (upstream) 8 end of the graft 1. The introducer sheath 4 is then withdrawn over the proximal (downstream) spring assembly 31. When the proximal (downstream) 9 end of the graft 1 is exposed it also expands under the action of the spring assembly 31 driving the barbs 10 (when present) into the wall of the aorta 2. The central control means 26 can then be withdrawn past the point where the central control means 26 engages the second set of mooring loops 39', thereby releasing the graft 1 completely. After the proximal (downstream) spring assembly 31 has been released, the tubular carrier 21, central control means 26, and introducer sheath 4 are removed from the patient's body. The femoral artery 30 is then repaired and the wound closed.

Figure 19:
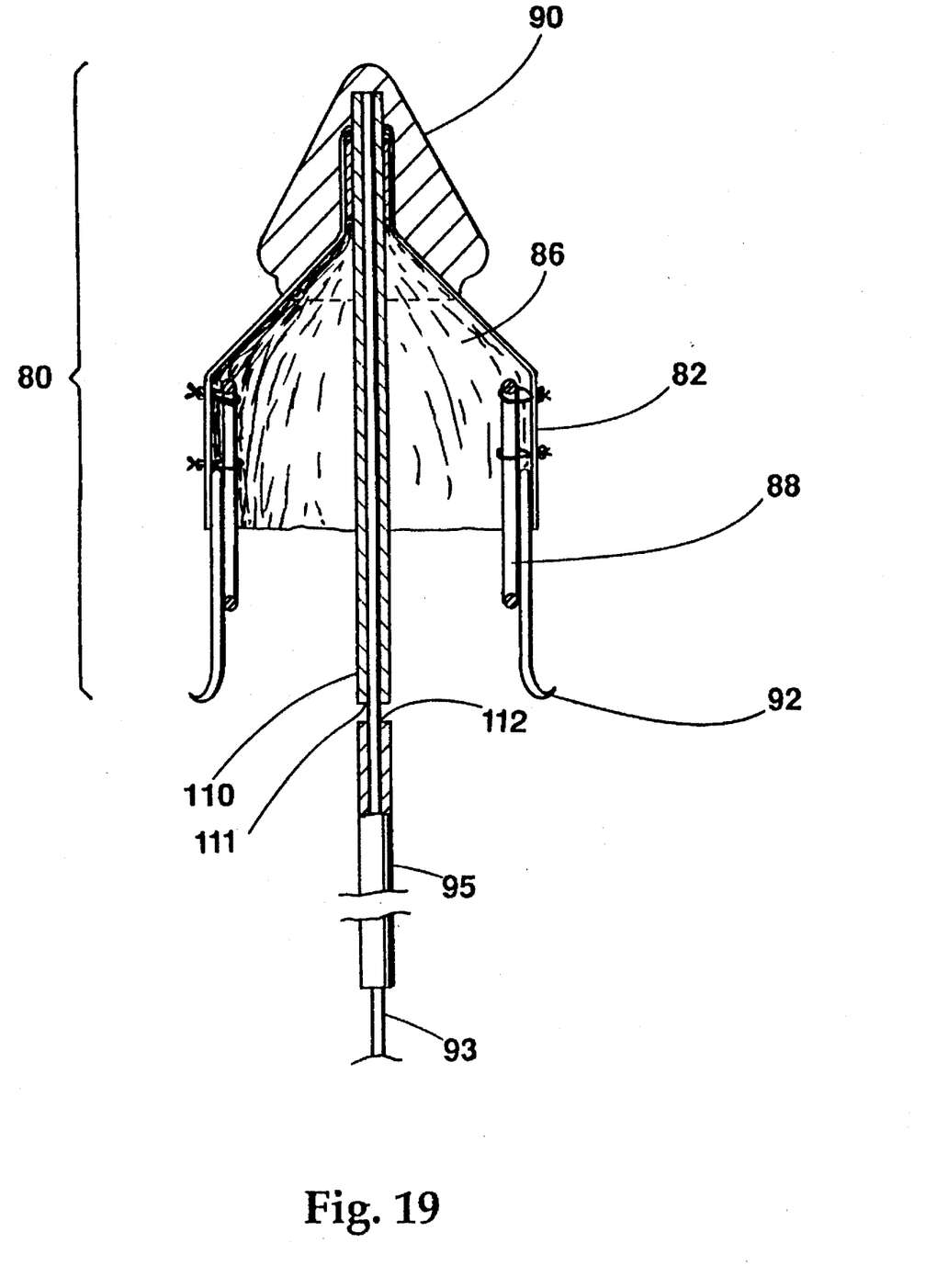
FIG. 19 is a longitudinal cross-sectional view of an occlusive umbrella.

Aortic aneurysms frequently encompass the entire distal aorta. In these cases, there is no normal aorta between the aneurysm and the iliac arteries. In order to provide a secure arterial wall for the attachment of the proximal (downstream) end of the graft, the graft may be placed from the infrarenal aorta, above the aneurysm, into the iliac artery on the side of insertion. Such an application also requires conventional femoro-femoral arterial bypass to restore continuity of the circulation to the contralateral limb and the insertion of an occlusive umbrella to prevent retrograde flow through the contralateral common iliac artery into the aneurysm. FIG. 19 is a longitudinal cross-sectional view of an occlusive umbrella 80. The graft 82 is open proximally, but closed distally, forming an inverted pocket 86, which is capped by a blunt tip dilator 90. A barbed 92 spring assembly 88 expands the open end of the graft 82. An umbrella catheter 110 having a longitudinal bore is attached to the inside of the dilator 90 and extends through the central axis of the umbrella 80. A pusher catheter 95 is abutted against the umbrella catheter 110 so that the longitudinal openings 111 and 112 are in alignment. A central pusher wire 93 is inserted through the longitudinal opening 112 of the pusher catheter 95 and through the longitudinal opening 111 of the umbrella catheter 110 until the central pusher wire 93 rests against the blunt tip dilator 90.

Figure 20:
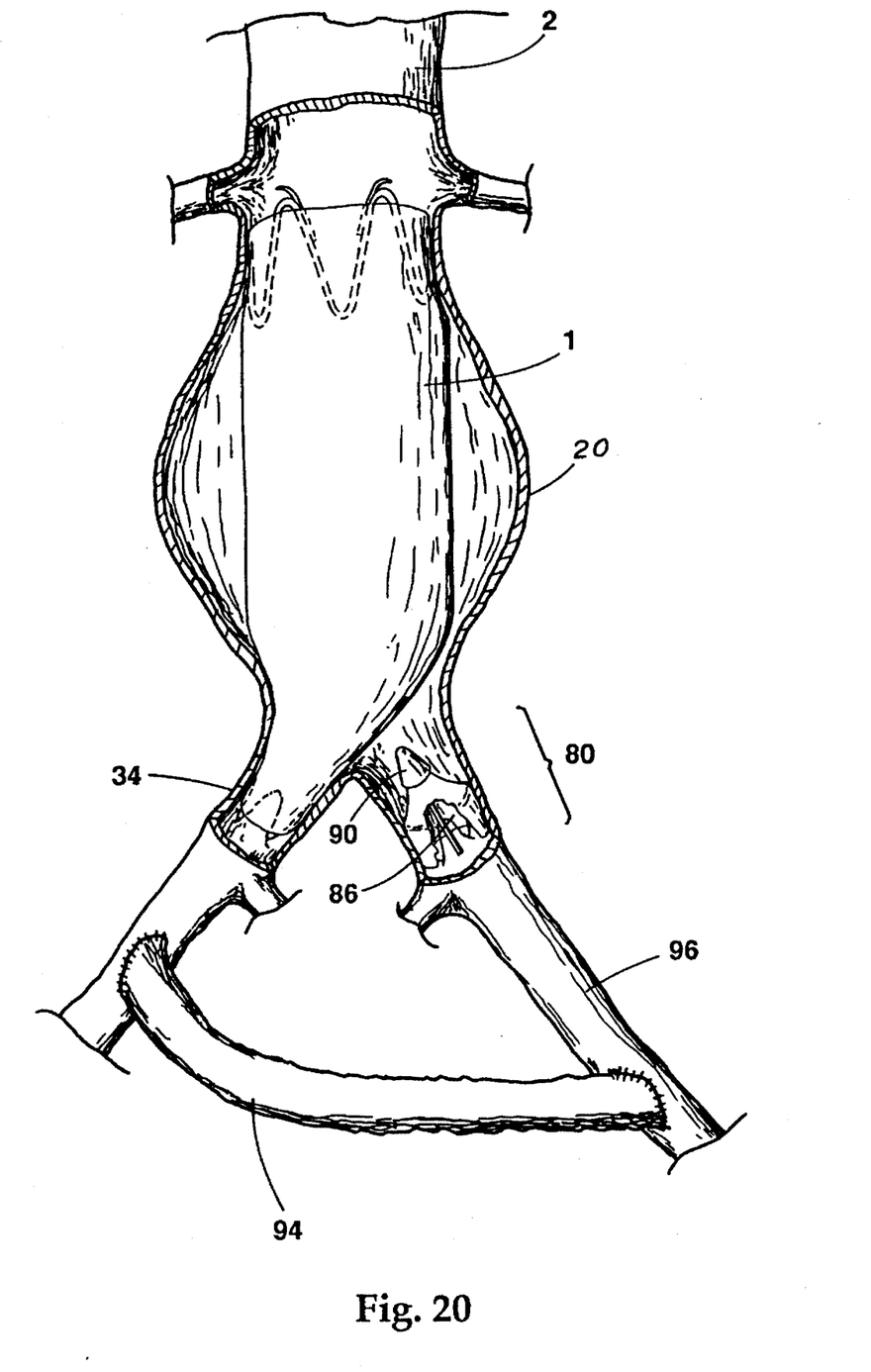
FIG. 20 is a longitudinal cross-sectional view of the aorta and the iliac arteries showing the use of a graft in conjunction with an occlusive umbrella and a femoro-femoral graft.

FIG. 20 shows an aneurysm 20 that extends from the aorta 2 to an iliac artery 34. The graft 1 is inserted so that it forms a conduit from the aorta 2 to the iliac artery 34. A conventional femoro-femoral bypass graft 94 is used to convey blood from the side receiving the entire aortic blood flow through the proximal end of the graft to the other limb. The occlusive umbrella 80 prevents arterial blood (which enters the iliac artery 34 via the femoro-femoral bypass 94) from "backing up" into the area between the graft 1 and the aneurysm 20.

Prior to insertion, the occlusive umbrella 80 is squeezed into the distal (upstream) end of the introducer sheath 4, until the introducer sheath 4 engages the blunt tip dilator 90 and the umbrella catheter 110 meets the pusher catheter 95. The umbrella catheter 110 and the pusher catheter 95 are kept in alignment by the central pusher wire 93 inserted through longitudinal openings 111 and 112. The apparatus is introduced into the femoral artery 30 through a longitudinal arteriotomy and advanced into the common iliac artery 34. The pusher 95 passes through the lumen of a flexible, thin walled, introducer sheath 4. The occlusive umbrella 80 is extruded from the introducer sheath 4 by applying force to the pusher 95 and central pusher wire 93 while pulling on the introducer sheath 4. Once the springs 88 and hooks 92 are out of the confines of the introducer sheath 4 they expand onto the arterial wall securing the umbrella 80. The pusher catheter 95, pusher wire 93, and introducer sheath 4 are then withdrawn from the femoral artery 30 through the arteriotomy. The arteriotomy is then anastomosed to the distal end of the femoro-femoral bypass 94.

When a "breech loading" introducer sheath is used, the sheath must first be inserted (over a dilator) through the femoral artery to the proximal end of the aneurysm. This can be done percutaneously or via an arteriotomy in the isolated femoral artery. The dilator is then removed, the sheath clamped, and the graft inserted. The graft is forced down the introducer sheath by a control catheter, wire or rod, which may traverse the lumen of the graft and attach the distal end of the graft to the control device or may end bluntly at the lower end of the graft. The latter requires that the graft be sufficiently rigid to withstand the compression necessary to overcome the considerable friction between the sheath and the graft.

I claim:

1. A device for grafting a prosthesis to a wall of a lumen, said device comprising:
   a) a tubular introducer sheath having a longitudinal bore;
   b) a prosthesis comprising a tubular graft having a longitudinal bore and disposed in the longitudinal bore of said tubular introducer sheath, said graft being expandable radially to substantially conform to an interior wall of a lumen;
      a self expanding spring assembly having a compressed state and attached to said tubular graft for expanding said graft so that it substantially conforms to an interior wall of a lumen after said introducer sheath has been removed from said self expanding spring assembly, said introducer sheath containing said self expanding spring assembly in said compressed state when said spring assembly is positioned in said longitudinal bore of said introducer sheath; and
      anchoring means for attaching said graft to an interior wall of a lumen;
   c) tubular carrier means having a longitudinal bore and disposed in the longitudinal bore of said tubular graft, said carrier means also having a plurality of apertures;
   d) central control means for maintaining an axial position of said prosthesis during removal of said introducer sheath, said central control means being disposed in the longitudinal bore of said tubular carrier means; and
   e) mooring loops engaging said prosthesis and passing through said apertures in said tubular carrier means to engage said central control means.

2. The device of claim 1 further comprising a dilator at one end of said tubular introducer sheath.

3. The device of claim 1 wherein said self expanding spring assembly comprises a plurality of spring frames.

4. The device of claim 3 wherein said spring frames are attached to the inside of said tubular graft.

5. The device of claim 3 wherein said spring frames are attached to the outside of said tubular graft.

6. The device of claim 1 wherein said anchoring means comprises a plurality of barbs.

7. The device of claim 1 wherein said central control means is a flexible catheter.

8. The device of claim 1 wherein said central control means is a thread.

9. A method for engrafting a prosthesis to a wall of a lumen comprising the steps of:
   a) providing an access to the lumen;
   b) providing a device for engrafting said prosthesis comprising:
      a tubular introducer sheath having a longitudinal bore;
      a tubular graft having a longitudinal bore and disposed in the longitudinal bore of said tubular introducer sheath, said graft being expandable radially to substantially conform to an interior wall of a lumen;
      a self expanding spring assembly having a compressed state and attached to said tubular graft for expanding said graft so that it substantially conforms to an interior wall of a lumen when said introducer sheath has been removed from said self expanding spring assembly, said introducer sheath containing said self expanding spring assembly in said compressed state when said spring assembly is positioned in said longitudinal bore of said introducer sheath;
      anchoring means for attaching said graft to an interior wall of a lumen;
      tubular carrier means having a longitudinal bore and disposed in the longitudinal bore of said tubular graft, said tubular carrier means also having a plurality of apertures;
      central control means for maintaining an axial position of said prosthesis during removal of said introducer sheath, said central control means being disposed in the longitudinal bore of said tubular carrier means; and
      mooring loops engaging said prosthesis and passing through said apertures in said tubular carrier means to engage said central control means;
   c) inserting said device into said access and urging said device to a desired location within the lumen;
   d) withdrawing said tubular introducer sheath to expose said prosthesis;
   e) allowing said self expanding spring assembly to self expand and substantially conform at least a portion of said graft to an interior wall of the lumen after said introducer sheath has been removed from said self expanding spring assembly;
   f) disengaging said central control means from said mooring loops; and
   g) removing said tubular introducer sheath, carrier means, and central control means.

10. A transluminal arrangement for positioning a prosthesis assembly at a particular position on a wall of a lumen, comprising:
   an introducer sheath having a longitudinal bore therein;
   a prosthesis assembly including a graft having a longitudinal bore and a self expanding spring assembly having a compressed state, said introducer sheath containing said self expanding spring assembly in said compressed state when said self expanding spring assembly is positioned in said longitudinal bore of said introducer sheath, said self expanding spring assembly radially expanding said graft to substantially conform said graft at a particular position on an interior wall of a lumen after said prosthesis assembly has been positioned in the lumen and said self expanding spring assembly has been released from said compressed state; and
   means positioned in said bore of said graft for retaining said prosthesis assembly at the particular position in the lumen when withdrawing said introducer sheath from said self expanding spring assembly and releasing said self expanding spring assembly from said compressed state.

11. The transluminal arrangement of claim 10 wherein said means for retaining comprises an elongated member having a dilator head at a distal end thereof, said head serving to facilitate penetration of said arrangement within the lumen and to minimize deleterious blood flow through the lumen during positioning of said arrangement.

12. The transluminal arrangement of claim 10 further comprising means for releasing said prosthesis assembly from said means for retaining after said introducer sheath has been withdrawn from said prosthesis assembly, 13. A method of transluminally positioning a prosthesis assembly at a particular position on an interior wall of a lumen, comprising the steps of:
   providing access to a lumen;
   providing an introducer sheath having a longitudinal bore;
   providing a prosthesis assembly positioned in said longitudinal bore of said introducer sheath and including a graft having a longitudinal bore and a self expanding spring assembly having a compressed state, said introducer sheath containing said self expanding spring assembly in said compressed state when said spring assembly is positioned in said longitudinal bore of said introducer sheath, said self expanding spring assembly radially expanding said graft to substantially conform said graft at a particular position on an interior wall of a lumen after said prosthesis assembly has been positioned in the lumen and said introducer sheath has been withdrawn from said prosthesis assembly releasing said self expanding spring assembly from said compressed state;

providing means positioned in said bore of said graft for retaining said prosthesis assembly at the particular position in the lumen;

positioning said introducer sheath and said prosthesis assembly positioned in said bore of said introducer sheath through said access to the particular position in the lumen; and withdrawing said introducer sheath from said prosthesis assembly positioned at the particular position in the lumen.

14. A transluminal arrangement for positioning at a particular position on a wall of a lumen a prosthesis assembly released from an introducer sheath, said transluminal arrangement comprising:

means for retaining said prosthesis assembly at the particular position in the lumen, said prosthesis assembly including a graft having a longitudinal bore and a self expanding spring assembly having a compressed state, said means for retaining being positioned in said bore of said graft, said introducer sheath containing said self expanding spring assembly in said compressed state when said spring assembly is positioned in said introducer sheath, said self expanding spring assembly radially expanding said graft to substantially conform said graft at a particular position on an interior wall of a lumen after said prosthesis assembly has been positioned in the lumen and said self expanding spring assembly has been released from said compressed state; and means for releasing said prosthesis assembly from said retaining means when positioned at the particular position in the lumen.

15. A transluminal arrangement for transluminally positioning a prosthesis assembly (1,12,31) of predetermined shape and size at a particular position on an internal wall (20) of a lumen, said prosthesis assembly comprising a graft (1) associated with a self expanding spring assembly (12,31) having a compressed state, said transluminal arrangement comprising an outer sheath (4) having a longitudinal bore for surrounding said prosthesis assembly when the latter is located at the particular position, and means (39,39',21, 26) for retaining said prosthesis assembly at the particular position while said outer sheath is being removed, characterized in that said retaining means has connected thereto an attachment arrangement (39,39') to be temporarily attached to said prosthesis assembly at least one position remote from a proximal end of said prosthesis assembly and in that said outer sheath maintains said self expanding spring assembly in said compressed state when said self expanding spring assembly is positioned in said longitudinal bore of said outer sheath.

16. The transluminal arrangement of claim 15, characterized in that said retaining means comprises an elongated member (21) to be extended within said prosthesis assembly, and in that said attachment arrangement is extended between said elongated member and said prosthesis assembly at said at least one position.

17. The transluminal arrangement of claim 16, characterized in that said elongated member is tubular and has a dilator head (22) at a distal end thereof, said head serving to facilitate penetration of said transluminal arrangement within the lumen and to minimize deleterious blood flow through the lumen during positioning of said prosthesis assembly.

18. The transluminal arrangement of claim 12, characterized in that a contraction arrangement (39, 39',21) is provided to temporarily pull said prosthesis assembly when said sheath is being withdrawn from said prosthesis assembly, and in that a disabling arrangement (26) is provided for releasing said prosthesis assembly either during or after removal of said sheath.

19. The transluminal arrangement of claim 18, characterized in that said contraction and disabling arrangements form part of said attachment arrangement, and in that part of said contraction and disabling arrangements are located and controlled within said elongated tubular member.

20. The transluminal arrangement of claim 19, characterized in that said attachment arrangement comprises at least one connector each in the form of sutures (39, 39') connected at one end to said prosthesis assembly and at the other end to inside of said elongated tube via apertures (29,101) and in that said disabling arrangement (26) is provided for releasing said sutures from inside said elongated tube.

21. The transluminal arrangement of claim 16, characterized in that said self expanding spring assembly comprises at least four barbs at a distal end of said spring assembly.

22. The transluminal arrangement of claim 16, characterized in that one end of said graft is sealed (80) to prevent flow of blood through the lumen.

23. An arrangement for transluminally positioning a prosthesis assembly at a particular position on an internal wall of a lumen, said assembly comprising a graft associated with self expanding spring apparatus having a compressed state, said arrangement comprising an outer sheath having a longitudinal bore for surrounding the said assembly when the latter is at the said particular position and for maintaining said self expanding spring apparatus in said compressed state when said self expanding spring apparatus is positioned in said longitudinal bore of said outer sheath, means for ensuring that the prosthesis assembly is maintained at the said particular position during removal of the outer sheath, said arrangement further comprising releasing means for disabling the ensuring means after the outer sheath has been withdrawn from the self expanding spring apparatus and released said self expanding spring apparatus from said compressed state and the prosthesis assembly has self expanded to the internal wall of the lumen at said particular position.

24. An arrangement for transluminally positioning a prosthesis assembly at a particular position on an internal wall of a lumen, said assembly comprising a graft associated with self expanding spring apparatus having a compressed state, said arrangement comprising an outer sheath having a longitudinal bore for surrounding the said assembly when the latter is at the said particular position, said outer sheath containing said self expanding spring apparatus in said compressed state when said spring apparatus is positioned in said longitudinal bore of said outer sheath, means for restraining axial movement of the prosthesis assembly during at least partial removal of the outer sheath, and means for disabling the restraining means after the outer sheath has been withdrawn from the self expanding spring apparatus and released said self expanding spring apparatus from said compressed state and the prosthesis assembly has self expanded to the said internal wall.

\* \* \* \* \*